US008684940B2

(12) United States Patent
Ashida

(10) Patent No.: US 8,684,940 B2
(45) Date of Patent: Apr. 1, 2014

(54) ELECTRONIC SPHYGMOMANOMETER WITH RECOMMENDED CUFF SITE ATTACHMENT DETECTION

(75) Inventor: Tameo Ashida, Takatsuki (JP)

(73) Assignee: Omron Healthcare Co., Ltd., Kyoto (JP)

( * ) Notice: Subject to any disclaimer, the term of this patent is extended or adjusted under 35 U.S.C. 154(b) by 260 days.

(21) Appl. No.: 13/112,313

(22) Filed: May 20, 2011

(65) Prior Publication Data

US 2011/0224561 A1  Sep. 15, 2011

Related U.S. Application Data

(63) Continuation of application No. PCT/JP2009/069191, filed on Nov. 11, 2009.

(30) Foreign Application Priority Data

Nov. 20, 2008  (JP) .................................. 2008-296508

(51) Int. Cl.
*A61B 5/021* (2006.01)
*A61B 5/022* (2006.01)
*A61B 5/023* (2006.01)
*A61B 5/0235* (2006.01)

(52) U.S. Cl.
USPC ........... 600/490; 600/301; 600/481; 600/489; 600/491; 600/492; 600/493; 600/494; 600/495; 600/496; 600/497; 600/498; 600/499

(58) Field of Classification Search
USPC .......................................... 600/301, 481–499
See application file for complete search history.

(56) References Cited

U.S. PATENT DOCUMENTS 5,752,913 A * 5/1998 Oka .............................. 600/300
6,464,646 B1 * 10/2002 Shalom et al. ................ 600/549

FOREIGN PATENT DOCUMENTS

| JP | 11-342117 A | 12/1999 |
| JP | 2007-054648 A | 3/2007 |
| JP | 2007-185233 A | 7/2007 |
| JP | 3140916 U | 4/2008 |
| RU | 2334455 | * 4/2006 |
| RU | 2334455 C2 | 9/2008 |
| WO | WO2007082593 | * 7/2007 ............. A61B 5/022 |

OTHER PUBLICATIONS

Eguchi et al., Consistency of Blood Pressure Differences Between the Left and Right Arms, Feb. 26, 2007, American Medical Association.*
Patents Abstracts of Japan, Publication No. 2007-185233, Publication Date: Jul. 26, 2007, 1 page.
Patents Abstracts of Japan, Publication No. 11-342117, Publication Date: Dec. 14, 1999, 1 page.
Patents Abstracts of Japan, Publication No. 2007-054648, Publication Date: Mar. 8, 2007, 1 page.

(Continued)

*Primary Examiner* — Jacqueline Cheng
*Assistant Examiner* — Puya Agahi
(74) *Attorney, Agent, or Firm* — Osha Liang LLP

(57) ABSTRACT

An electronic sphygmomanometer acquires a patient ID and recommended site information read from an ID card before measurement. The recommended site indicating the site to be attached to a cuff of a left site or a right site is thereby specified for every person to be measured (patient ID). Thereafter, the site to be attached to the cuff is guided by notifying the specified recommended site to the person to be measured.

8 Claims, 9 Drawing Sheets

(56) References Cited

OTHER PUBLICATIONS

International Search Report issued in PCT/JP2009/069191 mailed on Dec. 15, 2009, and an English translation thereof, 2 pages.

Office Action issued in corresponding Russian Application No. 2011124885/14(036758) dated Oct. 16, 2013, and English translation thereof (5 pages).

* cited by examiner

ELECTRONIC SPHYGMOMANOMETER WITH RECOMMENDED CUFF SITE ATTACHMENT DETECTION

TECHNICAL FIELD

The present invention relates to electronic sphygmomanometers, and in particular, to an electronic sphygmomanometer capable of measuring a blood pressure at a site on either left or right.

BACKGROUND ART

Conventionally, there is an electronic sphygmomanometer capable of measuring at a site either on the left or the right, but it is known that measurement accuracy may contain an error due to the difference in left and right of the site.

Japanese Unexamined Patent Publication Nos. 2007-185233 (Patent Document 1) and 11-342117 (Patent Document 2) disclose determining with which arm, left or the right, measurement is carried out, and displaying and printing a result in association with a blood pressure value. Whether the change in the blood pressure value is an error due to the difference in left and right then can be determined.

Conventionally, there is also an electronic sphygmomanometer that starts measurement after guiding to a correct measurement position. For example, Japanese Unexamined Patent Publication No. 2007-54648 (Patent Document 3) discloses calculating a shift in a measurement site and a heart position, and notifying by guidance so that the positions coincide.

Patent Document 1: Japanese Unexamined Patent Publication No. 2007-185233
Patent Document 2: Japanese Unexamined Patent Publication No. 11-342117
Patent Document 3: Japanese Unexamined Patent Publication No. 2007-54648

SUMMARY OF INVENTION

Even if with which arm, the left or the right, the measurement was carried out is displayed in association with the blood pressure value as in Japanese Unexamined Patent Publication Nos. 2007-185233 (Patent Document 1) and 11-342117 (Patent Document 2), the blood pressure cannot be appropriately managed unless the measurement is always carried out with one of the arms. If the measurement is carried out with the other arm even if informed by a doctor to measure with the specific arm, this may inhibit appropriate diagnosis.

Moreover, a sphygmomanometer that can guide to the correct measurement position exists as in Japanese Unexamined Patent Publication No. 2007-54648, but an electronic sphygmomanometer for guiding with which site on the left or the right to carry out the measurement does not exist.

Therefore, one or more embodiments of the present invention enables measurement to be carried out at the same site each time in an electronic sphygmomanometer capable of measuring at a site on either the left or the right.

According to one or more embodiments of the present invention, an electronic sphygmomanometer for measuring a blood pressure at a site on both left and right, includes a cuff for attaching to a left site or a right site; a specific processing unit for specifying a recommended site indicating a site to be attached to the cuff of the left site or the right site for every person to be measured; and a notification unit for notifying the recommended site specified by the specific processing unit.

According to one or more embodiments of the present invention, the electronic sphygmomanometer further includes a detection unit for detecting whether the site attached to the cuff is the left site or the right site; and a determination unit for determining whether or not the attached site matches the recommended site by comparing the recommended site specified by the specific processing unit and a detection result of the detection unit; wherein the notification unit further notifies a determination result of the determination unit.

According to one or more embodiments of the present invention, when it is determined by the determination unit that the sites do not match, the notification unit notifies information indicating that a site opposite to the attached site is to be attached to the cuff.

According to one or more embodiments of the present invention, the determination unit determines whether or not the attached site matches the recommended site until receiving an instruction to start measurement; and the notification unit notifies match or no-match until receiving the instruction to start the measurement.

According to one or more embodiments of the present invention, the electronic sphygmomanometer further includes a measurement processing unit for performing a process for measuring the blood pressure by adjusting a pressure in the cuff when receiving the instruction to start the measurement; and a storage unit for storing the blood pressure value measured by the measurement processing unit for every person to be measured.

According to one or more embodiments of the present invention, the storage unit stores identification information for identifying whether or not the site attached to the cuff during the process of the measurement processing unit is the recommended site in correspondence with the blood pressure value.

According to one or more embodiments of the present invention, the electronic sphygmomanometer further includes an output control unit for performing a control for outputting the measurement result by the measurement processing unit; wherein the output control unit outputs information for specifying whether or not the measurement is made by the recommended site in association with the measurement result based on the identification information.

According to one or more embodiments of the present invention, the electronic sphygmomanometer further includes a reading unit for reading information for specifying the person to be measured and information of the recommended site on the person to be measured recorded in a recording medium in advance; wherein the specific processing unit specifies the recommended site on the person to be measured based on the information read by the reading unit.

According to one or more embodiments of the present invention, the notification unit includes at least one of a display unit and an audio output unit.

According to one or more embodiments of the present invention, whether the site to be attached to the cuff is the left site or the right site is guided. Therefore, the person to be measured can carry out the measurement at the same site every time. As a result, the measurement result of the blood pressure useful for the diagnosis can be obtained.

DETAILED DESCRIPTION OF INVENTION

Figure 1:
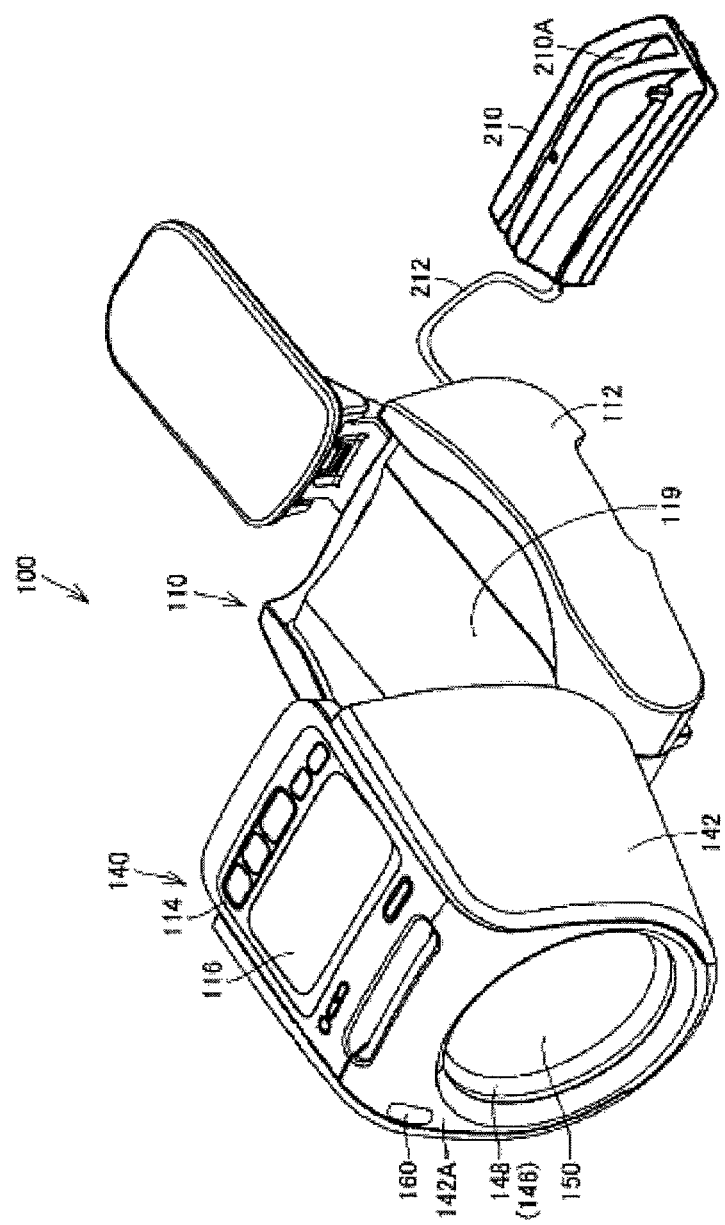
FIG. 1 is a perspective view showing an outer appearance when a sphygmomanometer according to an embodiment of the present invention is seen diagonally from the upper right side.

Embodiments of the present invention will be described in detail with reference to the drawings. The same reference numerals are denoted for the same or corresponding portions in the figures, and the description thereof will not be repeated.

An electronic sphygmomanometer (hereinafter simply referred to as "sphygmomanometer") in the present embodiment can measure a blood pressure at a site on either left or right.

(Regarding Outer Appearance and Configuration)

First, an outer appearance and a configuration example of a sphygmomanometer according to an embodiment of the present invention will be described.

FIG. 1 is a perspective view showing an outer appearance when a sphygmomanometer 100 according to the embodiment of the present invention is seen diagonally from the upper right side.

As shown in FIG. 1, the sphygmomanometer 100 according to the present embodiment mainly includes a main body 110 to be mounted on a mounting board such as a desk, and a living body inserting section 140 with a hollow opening 150, to which an upper arm of a subject is inserted. The main body 110 is covered by a main body casing 112, which is a first housing, and the living body inserting section 140 is covered by a living body inserting section casing 142, which is a second housing.

An elbow placement 119 for placing an elbow when the subject takes a measurement position is provided at a predetermined position at the upper surface of the main body 110. The elbow placement 119 is, for example, configured by forming a recess at the upper surface of the main body casing 112.

An operation unit 114 for accepting instructions from the subject, and a display unit 116 for displaying measurement results, operation guides, and the like are arranged at the upper surface of the living body inserting section 140. The operation unit 114 includes a power button used for turning the power ON, a measurement button for starting a measurement operation, a button for performing the operation of the display unit 116, and the like.

The living body inserting section 140 is rotatably coupled to the main body 110 by a rotation coupling mechanism including a rotation shaft. Specifically, the main body casing 112 and the living body inserting section casing 142 are rotatably coupled by a rotation shaft arranged in the main body casing 112 closer to the front side positioned on the subject side of the main body 110.

The living body inserting section 140 includes a cuff 146 arranged on the inner circumferential surface of the substantially cylindrical living body inserting section casing 142, and a cuff cover 148 attached to the living body inserting section casing 142 to cover the cuff 146.

A human body detection sensor 160 is arranged at a predetermined position near the hollow opening 150 on a front surface 142A of the living body inserting section casing 142. In the present embodiment, the human body detection sensor 160 is arranged at the position on the upper left of the hollow opening 150, and the like. Whether the right arm is inserted or the left arm is inserted can be determined by arranging the human body detection sensor 160 at such a position. That is, the site (hereinafter referred to as "attachment site") where the cuff 146 is attached is determined as the right arm if the existence of the human body is detected by the human body detection sensor 160 at the time of measurement, and the attachment site is determined as the left arm if the existence of the human body is not detected by the human body detection sensor 160.

The arrangement position of the human body detection sensor 160 is not limited to such a position as long as determination can be made on whether the attachment site is the right arm or the left arm. For example, the human body detection sensor 160 may be arranged on both the left side and the right side of the front surface 142A of the living body inserting section casing 142.

The human body detection sensor 160 is assumed as a pair of photoelectric sensors, but is not particularly limited as long as it can detect whether or not the human body exists within a predetermined range.

The sphygmomanometer 100 according to the present embodiment is installed in hospitals and the like, and has a function of identifying (specifying) a patient (person to be measured). Thus, the sphygmomanometer 100 includes a card reader 210 for reading information related to the person to be measured recorded on a recording medium such as an ID card, and a wiring 212 for electrically connecting the card reader 210 and the main body 110. The information related to the person to be measured will be described later. The card reader 210 includes an inserting portion 210A for inserting the ID card.

In the present embodiment, the sphygmomanometer 100 is a mounting type as shown in FIG. 1, but may also be a portable type. The site to be measured is the arm, but may be other sites that exist on the left and the right such as a wrist.

Figure 2:
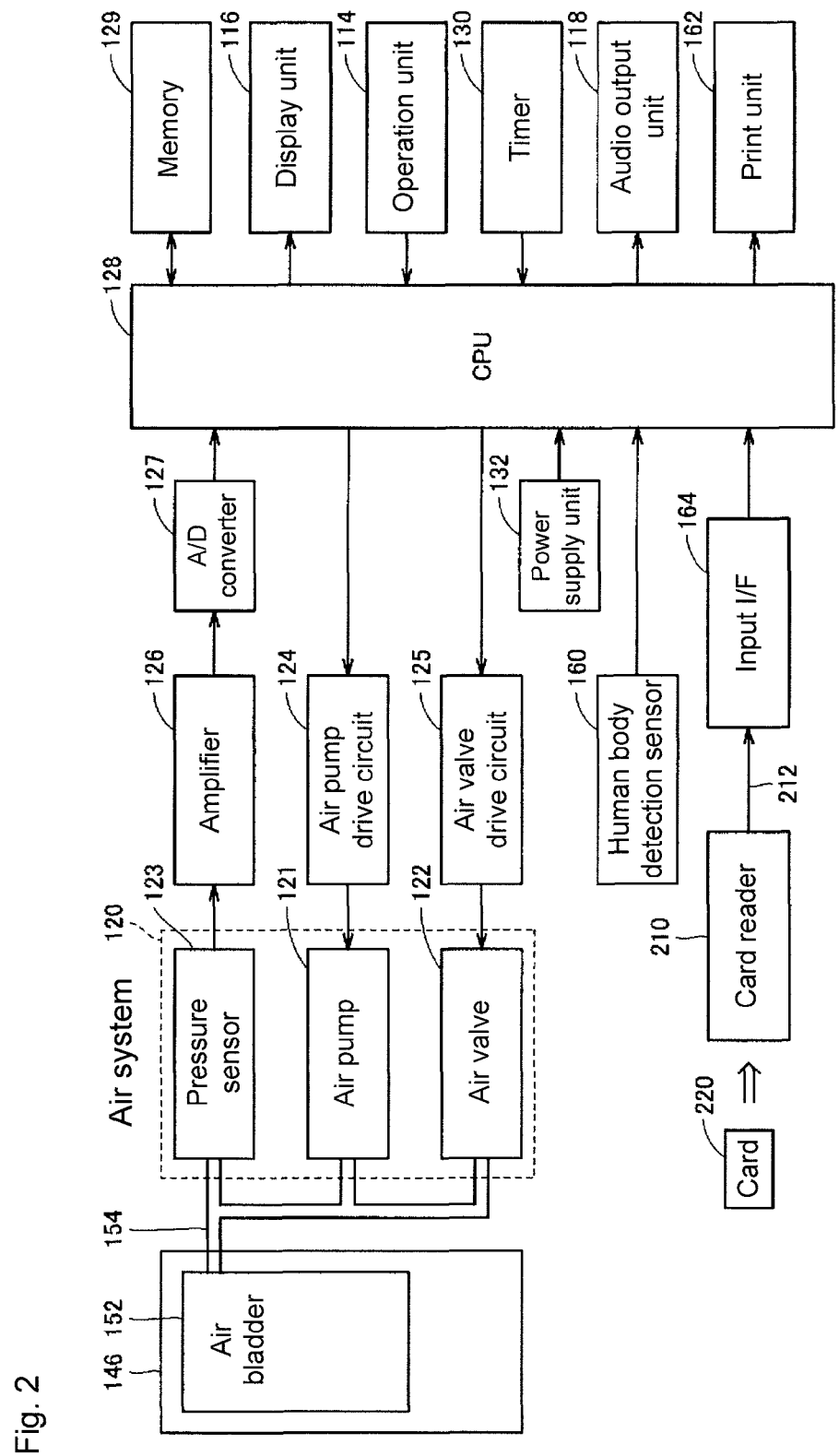
FIG. 2 is a hardware block diagram showing a configuration of a sphygmomanometer according to the embodiment of the present invention.

FIG. 2 is a hardware block diagram showing a configuration of the sphygmomanometer 100 according to the embodiment of the present invention.

As shown in FIG. 2, in addition to the operation unit 114, the display unit 116, and the human body detection sensor 160, the sphygmomanometer 100 includes an air bladder 152 incorporated in the cuff 146, a pressure sensor 123 for detecting the pressure (hereinafter referred to as "cuff pressure") in the air bladder 152, an amplifier 126 for amplifying the signal detected by the pressure sensor 123, an A/D converter 127 for converting the amplified analog signal to a digital signal, an air pump 121 and an air valve 122 for adjusting the level of the cuff pressure, an air pump drive circuit 124 for driving the air pump 121, an air valve drive circuit 125 for adjusting the opening/closing degree of the air valve 122, a CPU (Central Processing Unit) 128 for intensively controlling and monitoring each unit, a memory 129 for storing various types of data and programs, a timer 130 for performing the timing operation and outputting the timed data, a power supply unit 132, an audio output unit 118 for outputting audio, a print unit 162 for printing the measurement result and the like on a paper medium, and an input I/F (interface) 164 for inputting the information read by the card reader 210. The information inputted by the input I/F 164 is provided to the CPU 128.

As described above, the air bladder 152 is connected to an air system 120 including an air pump 121, an air valve 122, and a pressure sensor 123 with an air tube 154.

The CPU 128 is connected to the A/D converter 127, the air pump drive circuit 124, the air valve drive circuit 125, the memory 129, the display unit 116, the operation unit 114, the audio output unit 118, the timer 130, the power supply unit 132, the human body detection sensor 160, the print unit 162, and the input I/F 164.

In the sphygmomanometer 100 of the present embodiment, all devices other than the air bladder 152, the operation unit 114, the display unit 116, the audio output unit 118, and the human body detection sensor 160 are arranged in the main body 110, and are accommodated in the main body casing 112. The air bladder 152, the air pump 121, the air valve 122, and the pressure sensor 123 are connected with a flexible air tube. The operation unit 114, the display unit 116, the audio output unit 118, the human body detection sensor 160, and the CPU 128 are connected by a flexible signal line. Injection and discharge of air or transmission and reception of a signal can be carried out while following the rotational movement of the living body inserting section casing 142 by connecting the devices accommodated in the main body casing and the devices accommodated in the living body inserting section casing 142 using the flexible air tube and the signal line.

The sphygmomanometer 100 may further include a beeper that issues a warning sound or the like.

Figure 3:
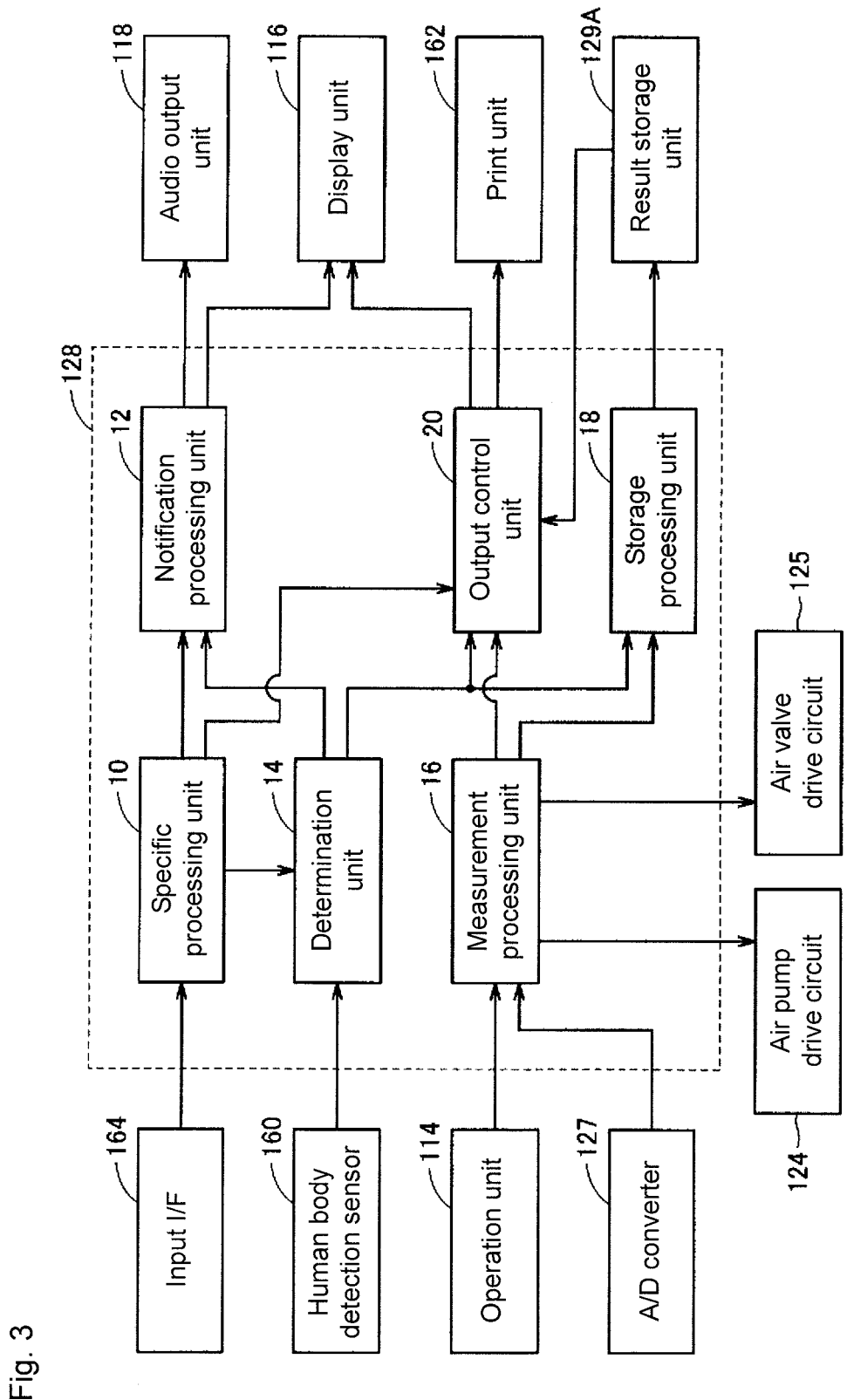
FIG. 3 is a function block diagram showing a function configuration of the sphygmomanometer according to the embodiment of the present invention.

FIG. 3 is a function block diagram showing the function configuration of the sphygmomanometer 100 according to the embodiment of the present invention. In FIG. 3, only the peripheral hardware that directly exchanges signals with each unit of the CPU 128 is shown to simplify the description.

With reference to FIG. 3, the sphygmomanometer 100 includes a specific processing unit 10, a notification processing unit 12, a determination unit 14, a measurement processing unit 16, a storage processing unit 18, and an output control unit 20 as functions thereof.

The specific processing unit 10 specifies the target person to be measured of a plurality of people to be measured before the measurement, and specifies the site to be attached (hereinafter referred to as "recommended site") to the cuff 146 of the left arm (left site) and the right arm (right site). Thus, the recommended site is specified for every person to be measured. Specifically, the specific processing unit 10 specifies the target person to be measured and the recommended site in the following manner. In other words, the person to be measured passes the ID card 220 he or she possesses through the inserting portion 210A of the card reader 210, so that the card reader 210 reads the information related to the person to be measured, that is, the information for specifying the person to be measured and the information of the recommended site recorded in advance in the ID card 220. The "information for specifying the person to be measured" is, for example, a patient ID. The "information of the recommended site" is the left and right identifying information for identifying the left and the right of the site, and indicates left or right. The information of the recommended site is recorded in the ID card by a medical staff such as a doctor. For example, for the person to be measured subjected to artificial dialysis, the site not subjected to dialysis is recorded as the recommended site. Such information may be recorded to the ID card by a known method.

The information related to the person to be measured read by the card reader 210 is outputted to the specific processing unit 10 through the input I/F 164. The specific processing unit 10 specifies the target person to be measured and the recommended site based on the received information related to the person to be measured.

In the present embodiment, the person to be measured is specified using the ID card 220, but embodiments of the present invention are not limited thereto. For example, the person to be measured may be specified by the input of the patient ID by a user. In this case, the information of the recommended site is assumed to be stored in advance in correspondence with each patient ID in a predetermined region of the memory 129.

The notification processing unit 12 performs a process of notifying the recommended site specified by the specific processing unit 10. The arm to be attached (inserted) is thus guided to the person to be measured. The notification processing unit 12 also performs a process of further notifying the determination result by the determination unit 14, to be described later. If determined to be not matched by the determination unit 14, the notification processing unit 12 notifies the information that the site opposite to the recommended site is to be attached to the cuff 146.

The method of notification by the notification processing unit 12 may be performed by display or by audio output.

The determination unit 14 determines the attachment site based on the signal from the human body detection sensor 160. Whether or not the attachment site matches the recommended site is determined by comparing the recommended site specified by the specific processing unit 10 and the detection result by the human body detection sensor 160. The determination unit 14 determines whether or not the attachment site matches the recommended site until the instruction to start the measurement is accepted. The match/no match of the site are thus notified by the notification processing unit 12 until the instruction to start the measurement is accepted.

The measurement processing unit 16 performs a process of measuring the blood pressure by adjusting the pressure of the cuff 146 when the instruction to start the measurement is accepted. The process by the measurement processing unit 16 may be realized by a known method. The measurement processing unit 16 is connected with the air pump drive circuit 124, the air valve drive circuit 125, and the A/D converter 127, and measures the systolic blood pressure and the diastolic blood pressure by an oscillometric method.

The storage processing unit 18 stores the blood pressure value measured by the measurement processing unit 16 in a result storage unit 129A in association with the specified target person to be measured. In this case, the identification information for identifying whether or not the site attached to the cuff 146 during the process by the measurement processing unit 16 is the recommended site is stored in correspondence with the blood pressure value. The result storage unit 129A is arranged in the memory 129. The memory 129 is a non-volatile memory and is for example, a flash memory.

In the present embodiment, the measurement result is recorded in the memory 129 of the sphygmomanometer 100, but embodiments of the present invention are not limited thereto. For example, the measurement result may be recorded in a removable recording medium by a drive device (not shown) or may be transmitted to an external computer through a network (not shown) as long as the measurement result is stored in correspondence with the patient ID (identification information of person to be measured).

The output control unit 20 performs a control to output the measurement result by the measurement processing unit 16.

In this case, the information for specifying whether or not measured by the recommended site based on the identification information is outputted in association with the measurement result.

The method of outputting by the output control unit 20 may be performed by display or by printing.

The operation of the function blocks described above may be realized by executing the software stored in the memory 129 or at least one may be realized by hardware.

(Regarding Operation and Display Example)

The specific operation and display example of the sphygmomanometer 100 according to the embodiment of the present invention will now be described.

Figure 4:
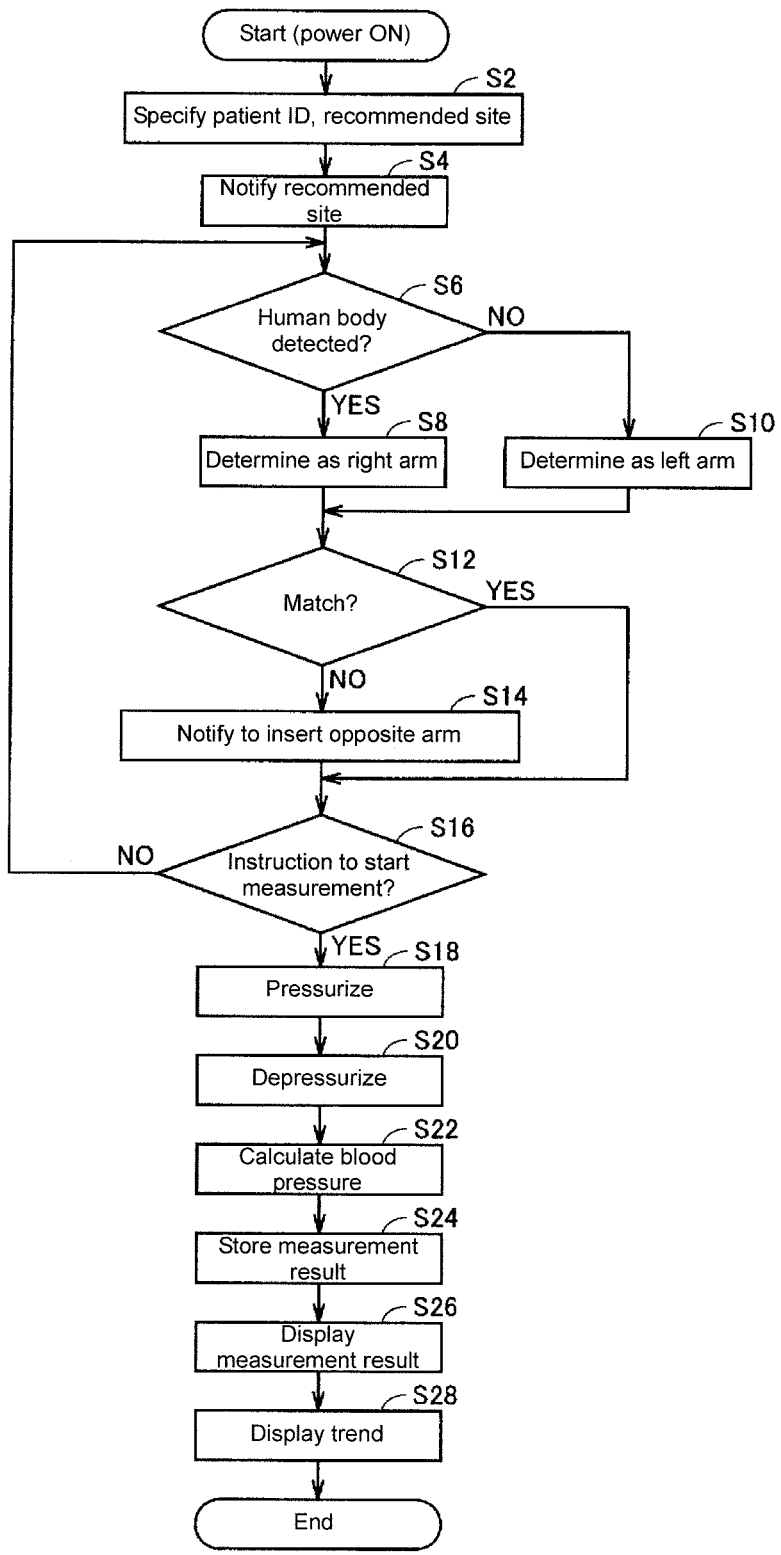
FIG. 4 is a flowchart showing a process (blood pressure measuring and recording process) executed when power is turned ON or the like in the sphygmomanometer according to the embodiment of the present invention.

FIG. 4 is a flowchart showing a process (hereinafter referred to as "blood pressure measuring and recording process") executed when the power is turned ON or the like in the sphygmomanometer 100 according to the embodiment of the present invention. The processes shown in the flowchart of FIG. 4 are stored in the memory 129 as a program in advance, so that the functions of the blood pressure measurement and recording process are realized when the CPU 128 reads out and executes the program.

With reference to FIG. 4, when the power is turned ON, the specific processing unit 10 of the CPU 128 first specifies the patient ID and the recommended site (left arm or right arm) (step S2). Specifically, the patient ID and the recommended site information the card reader 210 read from the ID card 220 are acquired through the input I/F 164. The recommended site of the person to be measured identified with the patient ID is thereby specified. The information on the specified patient ID and the recommended site is temporarily recorded in the internal memory.

The notification processing unit 12 of the CPU 128 then notifies the recommended site (step S4). Specifically, whether the recommended site, i.e., the site to be attached is the left arm or the right arm is displayed. The display example of the recommended site is shown in FIG. 5.

Figure 5:
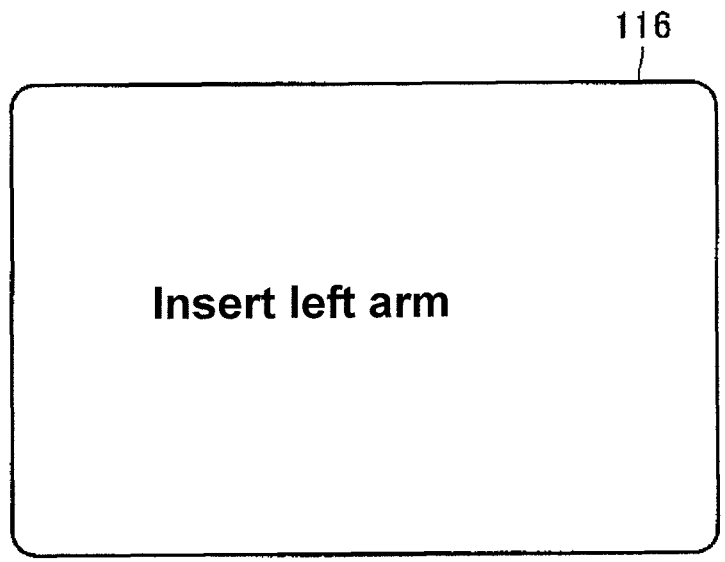
FIG. 5 is a view showing a display example of a recommended site in step S4 of FIG. 4.

With reference to FIG. 5, if the recommended site is the left arm, a message "insert left arm" is displayed on the display unit 116.

The determination unit 14 then determines whether or not the human body is detected based on the signal from the human body detection sensor 160 (step S6). If it is determined that the human body is detected (YES in step S6), the attachment site is determined as the right arm (step S8). If the human body is not detected (NO in step S6), the attachment site is determined as the left arm (step S10).

Thereafter, the determination unit 14 determines whether or not the attachment site matches the recommended site (step S12). If it is determined that the sites match (YES in step S12), the process proceeds to step S16. If it is determined that the sites do not match (NO in step S12), the notification processing unit 12 makes a notification to insert the arm opposite to the attachment site (step S14). Specifically, a screen shown in FIG. 6 is displayed on the display unit 116.

Figure 6:
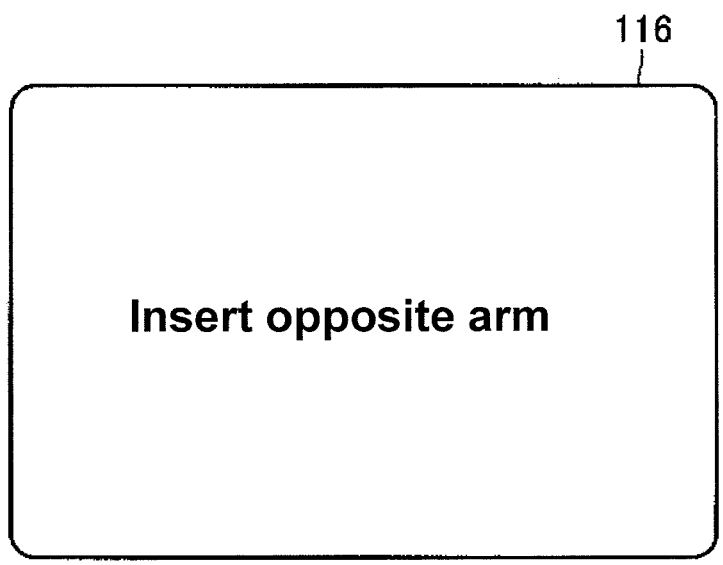
FIG. 6 is a view showing a display example in step S14 of FIG. 4.

With reference to FIG. 6, a message "insert opposite arm" is displayed on the display unit 116. The person to be measured then can recognize that the inserted arm is the wrong arm and can reattach to the arm appropriate for the measurement. Thus, even with a healthy person to be measured such as a person not subjected to artificial dialysis, the error due to the left and right difference can be eliminated by guiding which of the left and right arms should be measured.

In step S14, the above message may be outputted in audio from the audio output unit 118 in addition to or in place of the display of FIG. 6. Alternatively, a warning sound may be issued from the beeper.

The process proceeds to step S16 after the process of step S14 is finished.

In step S16, the CPU 128 determines whether or not the instruction to start the measurement is inputted by the user (representatively person to be measured) (step S16). Specifically, whether or not the measurement button in the operation unit 114 is pushed is determined. If the instruction to start the measurement is not made (NO in step S16), the process returns to step S6. The above processes by the determination unit 14 and the notification processing unit 12 are then repeated.

In the present embodiment, even if the attachment site and the recommended site match, the determination of the attachment site by the determination unit 14 is continuously carried out until the instruction to start the measurement is inputted, but when the sites are matched, the input of the instruction to start the measurement may be waited. That is, the process may not return to the process of step S6. This is because, once either one of the arms is inserted, it is unlikely that the opposite arm will be reattached unless notification is made to insert the opposite arm in step S14.

Moreover, notification may be made that the attachment site is correct if the attachment site and the recommended site match.

When the instruction to start the measurement is inputted by the user (YES in step S16), the process proceeds to the blood pressure measurement process. The measurement processing unit 16 starts to drive the air pump drive circuit 124 and performs a pressurization process of gradually raising the cuff pressure (step S18). The measurement processing unit 16 stops the air pump drive circuit 124 when the cuff pressure reaches a predetermined level for blood pressure measurement in the process of gradually pressurizing.

The measurement processing unit 16 gradually depressurizes the cuff pressure by controlling the air valve drive circuit 125 (step S20), and calculates the blood pressure (systolic blood pressure, diastolic blood pressure) and the pulse rate by a known method (step S22). Specifically, the measurement processing unit 16 extracts pulse wave information based on the signal obtained from the A/D converter 127 in the process of gradually depressurizing the cuff pressure. The blood pressure is calculated from the extracted pulse wave information.

The blood pressure is measured in the fine speed depressurization process of the cuff pressure in the present embodiment, but the blood pressure may be measured in the pressurization process of the cuff pressure.

After the measurement of the blood pressure is finished, the storage processing unit 18 records the measurement results in the result storage unit 129A of the memory 129 in correspondence with the patient ID of the person to be measured this time (step S24). In this case, the measured blood pressure data (and pulse rate data) and the information for identifying match/no-match of the sites are stored in correspondence.

Figure 7:
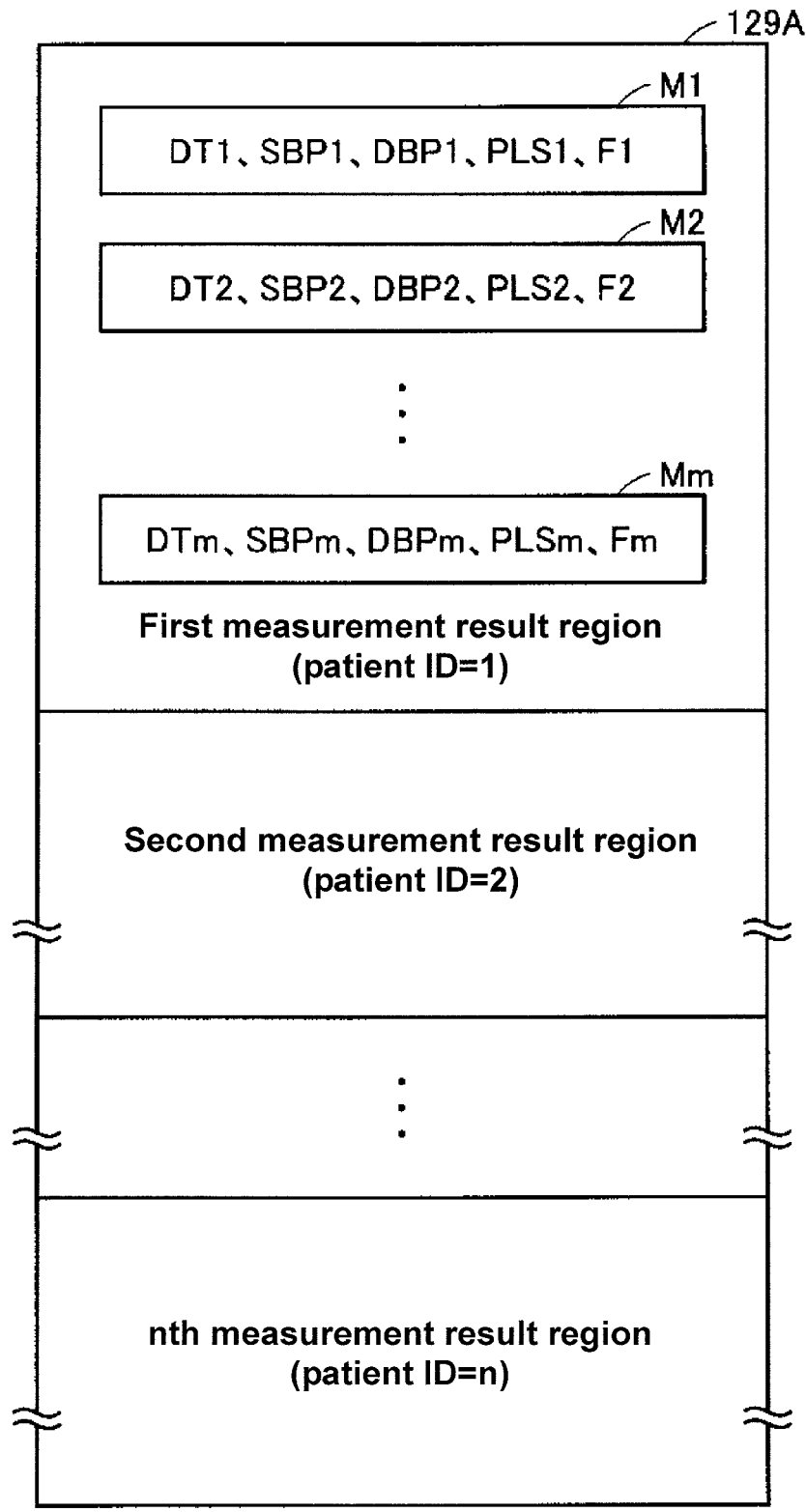
FIG. 7 is a view showing one example of a data structure of a result storage unit of a memory.

FIG. 7 is a view showing one example of a data structure of the result storage unit 129A of the memory 129.

With reference to FIG. 7, the result storage unit 129A includes a measurement result region for every patient ID. Each measurement result region stores measurement result data M1 to Mm (m=1, 2, 3, . . . ) for every measurement. Each measurement result data includes measurement date and time data DT, systolic blood pressure data SBP indicating the systolic blood pressure, diastolic blood pressure data DBP indicating the diastolic blood pressure, pulse rate data PLS indicating the pulse rate, and identification flag F indicating match/no-match of the sites.

The identification flag F is information for identifying whether or not the attachment site matches the recommended site (whether measured with the appropriate arm). The identification flag F indicates "0" if matched and "1" if not matched, for example.

The measurement value and the identification flag merely need to be stored in correspondence to each other and are not limited to the storage form using records.

In the present embodiment, the recommended site is notified and notification is made to insert the correct arm if the attachment site is wrong, but the measurement may not necessarily be made at the recommended site. For example, the arm to be attached may not be used for measurement due to injury, or the like. Accordingly, the arrangement of the identification flag F in the measurement result data is useful in the subsequent diagnosis.

The output control unit 20 then displays the measurement result on the display unit 116 (step S26). The display example of the measurement result is shown in FIG. 8.

Figure 8:
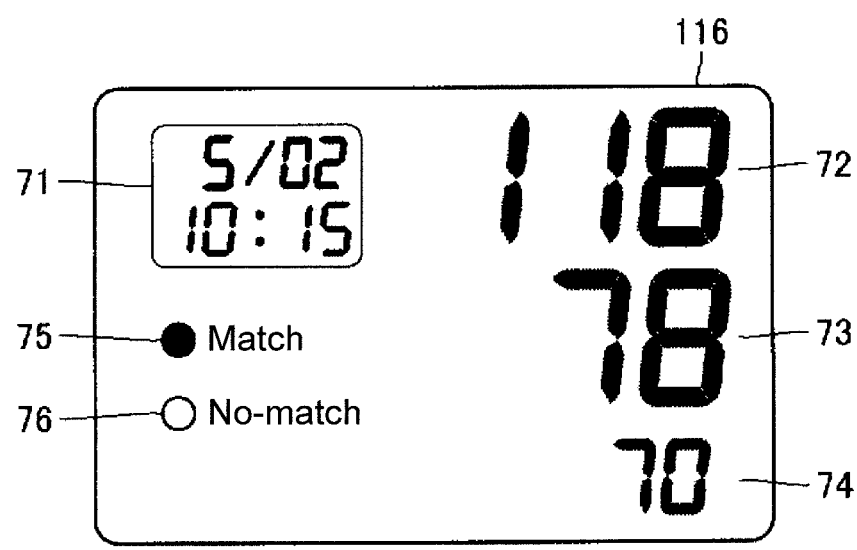
FIG. 8 is a view showing a display example of the measurement result in step S26 of FIG. 4.

With reference to FIG. 8, the measurement date and time is displayed in a region 71 of the display unit 116. The measurement date and time correspond to the time point at which instruction to start the measurement is inputted. Regions 72, 73, 74 of the display unit 116 display the systolic blood pressure, the diastolic blood pressure, and the pulse rate calculated in step S22 of FIG. 4, respectively.

The display unit 116 also includes a check box 75 filled if the sites match and a check box 76 filled if the sites do not match. Whether the displayed measurement result is for a state in which the attachment site and the recommended site match (whether measured under appropriate condition) can be notified to the user and the medical staff. As a result, the medical staff can easily determine whether the measurement result is reliable.

Embodiments of the present invention are not limited to such an example as long as the match/no-match of the sites can be specified, and for example, a predetermined mark may be displayed only for no-match.

The output control unit 20 may print information (e.g., predetermined mark or the like) for specifying match/no-match of the sites when printing the measurement result.

Figure 9:
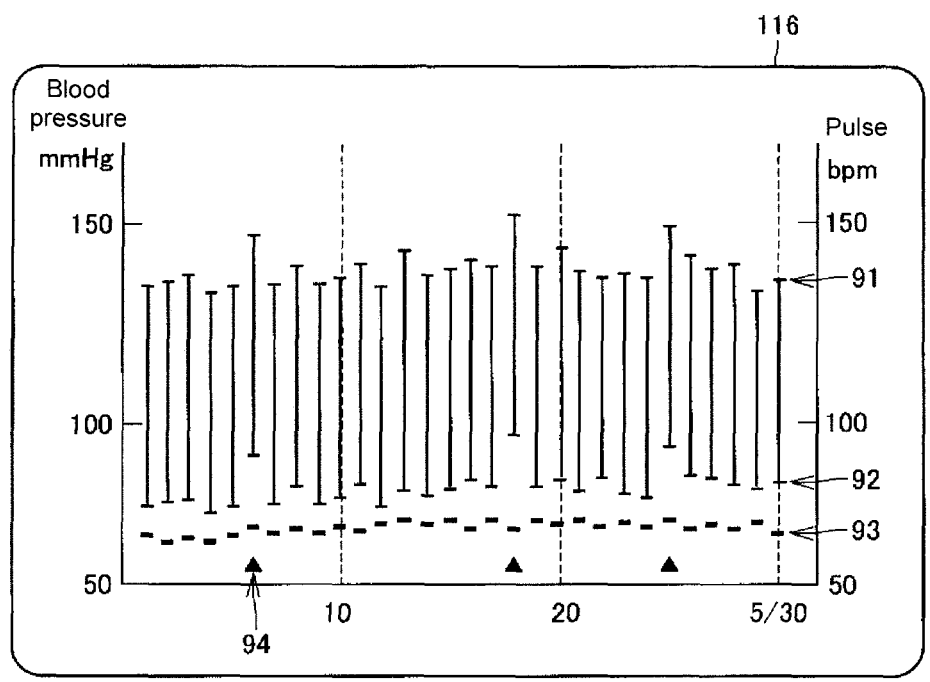
FIG. 9 is a view showing a display example of a trend in step S28 of FIG. 4.

Lastly, the output control unit 20 displays the trend of the measurement results for a plurality of times of measurement (step S28). Specifically, the output control unit 20 reads out a plurality of (e.g., immediate predetermined number of times) measurement result data stored in the measurement result region of the target patient ID in the result storage unit 129A. Then, a trend graph as shown in FIG. 9 is displayed. FIG. 9 is a view showing a display example of the trend.

With reference to FIG. 9, the display unit 116 displays a graph where the blood pressure (unit: mmHg) and the pulse (unit: bpm) are shown on the vertical axis, and the date is shown on the horizontal axis. In such a graph, a mark 91 representing the systolic blood pressure is shown at the position of the systolic blood pressure value, a mark 92 representing the diastolic blood pressure is shown at the position of the diastolic blood pressure value, and a mark 93 representing the pulse is shown at the position of the pulse rate for every measurement date. A predetermined mark 94 is displayed in association with the marks 91, 92, 93 of the measurement value for the measurement result in which the identification flag F is "1" (no-match) of each measurement result data. With the display of such a mark 94, the information useful for the medical staff to understand the change of the systolic blood pressure and the diastolic blood pressure for every day can be provided. That is, even if the systolic blood pressure and the diastolic blood pressure indicate abnormal values on a certain measurement date, determination can be made as an error due to mistake in the attachment site if the measurement data has the mark 94.

The blood pressure measurement and storage process in the present embodiment is thereby finished.

The executing order of the processes of steps S24, S26, S28 of FIG. 4 is not limited.

Therefore, because the recommended site is notified before the measurement is started according to the present embodiment, the person to be measured does not hesitate which arm to insert. Furthermore, measurement can be made at any time with the same arm.

Furthermore, if the actually inserted arm differs from the recommended site, notification is made to insert the opposite arm. Thus, the person to be measured can re-insert the arm appropriate for the measurement even if the arm different from the recommended site is inserted.

However, the measurement may not be made with the recommended site due to the body condition (e.g., injury) at the time of the measurement, and thus, the sphygmomanometer 100 of the present embodiment enables the measurement to be carried out even with the arm different from the recommended site. Thus, the identification flag F is stored in correspondence with the measurement value (systolic blood pressure, diastolic blood pressure). Information indicating whether or not the result measured with the recommended site is outputted when outputting the measurement result. The medical staff thus can easily determine whether the result is reliable or not.

In particular, determination can be easily made on the cause of the change in blood pressure value for patients having bilateral difference by displaying the mark 94 on the trend graph. As a result, appropriate diagnosis and blood pressure management can be achieved.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

DESCRIPTION OF REFERENCE NUMERALS 10 specific processing unit
12 notification processing unit
14 determination unit
16 measurement processing unit
18 storage processing unit
20 output control unit
100 sphygmomanometer
110 main body
112 main body casing
114 operation unit
116 display unit
118 audio output unit
120 air system
121 air pump
122 air valve
123 pressure sensor
124 air pump drive circuit
125 air valve drive circuit
126 amplifier
127 A/D converter
128 CPU
129 memory
129A result storage unit 130 timer
132 power supply unit
140 living body inserting section
142 living body inserting section casing
146 cuff
148 cuff cover
150 hollow opening
152 air bladder
154 air tube
160 human body detection sensor
162 print unit
210 card reader
212 wiring
220 ID card
164 input I/F

The invention claimed is:

1. An electronic sphygmomanometer for measuring a blood pressure value at a left measurement site and a right measurement site, the electronic sphygmomanometer comprising:
 a cuff that attaches to the left measurement site or the right measurement site;
 a specific processing unit that specifies a recommended site indicating one of the left measurement site or the right measurement site for attachment of the cuff for every person to be measured;
 a notification unit that notifies a user of the recommended site specified by the specific processing unit;
 a detection unit that detects whether the cuff is attached to the left measurement site or the right measurement site, wherein the left measurement site or the right measurement site that the cuff is attached to is an attached site; and
 a determination unit that determines whether or not the attached site matches the recommended site by comparing the recommended site specified by the specific processing unit and a detection result of the detection unit,
 wherein the notification unit further notifies a determination result of the determination unit.

2. The electronic sphygmomanometer according to claim 1, wherein when determined by the determination unit that the sites do not match, the notification unit notifies information indicating that the cuff is to be attached to a site opposite to the attached site.

3. The electronic sphygmomanometer according to claim 1,
 wherein the determination unit determines whether or not the attached site matches the recommended site until receiving an instruction to start measurement, and
 wherein the notification unit notifies match or no-match until receiving the instruction to start the measurement.

4. The electronic sphygmomanometer according to claim 3, further comprising:
 a measurement processing unit that performs a process that measures the blood pressure value by adjusting a pressure in the cuff when receiving the instruction to start the measurement; and
 a storage unit that stores the blood pressure value measured by the measurement processing unit for every person to be measured.

5. The electronic sphygmomanometer according to claim 4, wherein the storage unit stores identification information for identifying that identifies whether or not the site attached to the cuff during the process of the measurement processing unit is the recommended site in correspondence with the blood pressure value.

6. The electronic sphygmomanometer according to claim 5, further comprising:
 an output control unit that performs a control for outputting a measurement result by the measurement processing unit,
 wherein the output control unit outputs information that specifies whether or not the measurement is made at the recommended site in association with the measurement result based on the identification information.

7. The electronic sphygmomanometer according to claim 1, further comprising:
 a reading unit that reads information that specifies the person to be measured and information of the recommended site on the person to be measured recorded in a recording medium in advance,
 wherein the specific processing unit specifies the recommended site on the person to be measured based on the information read by the reading unit.

8. The electronic sphygmomanometer according to claim 1, wherein the notification unit includes at least one of a display unit and an audio output unit.

* * * * *